Nov. 30, 1954 F. W. ANDERSON Plant Pat. 1,326

NECTARINE TREE

Filed March 29, 1954

WITNESS

Addison E. Avery

INVENTOR

Frederic W. Anderson

Webster & Webster

ATTYS.

United States Patent Office

Plant Pat. 1,326

Patented Nov. 30, 1954

1,326

NECTARINE TREE

Frederic W. Anderson, Merced, Calif.

Application March 29, 1954, Serial No. 419,629

1 Claim. (Cl. 47—62)

This invention is directed to a new and distinct variety of nectarine tree; the variety having been originated by me in my experimental nursery and orchard near Merced, California, during the course of a long and continuing nectarine breeding program seeking improved varieties for commercial growing.

The John Rivers nectarine (unpatented) was introduced from England by the United States Department of Agriculture, and first planted in California in the early 1930's. Despite rather soft flesh, which is white in color, the John Rivers nectarine has become a leading commercial variety in the State of California, largely by reason of its early ripening period—to-wit, in late June in such region.

The principal object of the present invention was to originate a nectarine tree having freestone fruit which is larger, firmer, and yellow fleshed, but having the same harvest period as said John Rivers nectarine; such object having been successfully accomplished by me in the following manner:

The Le Grand nectarine (United States Plant Patent No. 549) was crossed with the Halehaven peach (unpatented); it having been previously determined that selfed progeny of the Halehaven peach ripened over a relatively long period of about six weeks. The F–1 progeny of the Le Grand nectarine × Halehaven peach cross, as above, were all peach trees which bore yellow fleshed fruit; the latter having certain variations which I observed.

Open pollenated seeds of the most desirable of such progeny, particularly the early ripening ones, were planted. Approximately 25% of these plantings produced nectarine trees having yellow fleshed fruit, and the most promising were top-worked in orchard trees for further testing and observation.

The herein claimed variety of nectarine tree was selected from such top workings as being of especial promise because of the large size, attractive external color, firmness of flesh, and time of ripening of the fruit, which ripening period is approximately with the John Rivers nectarine.

Subsequent to its origination the variety has been successfully asexually reproduced by top working on mature trees in my orchard located as aforesaid; the reproductions having been found to run true in all respects.

Figure 1:
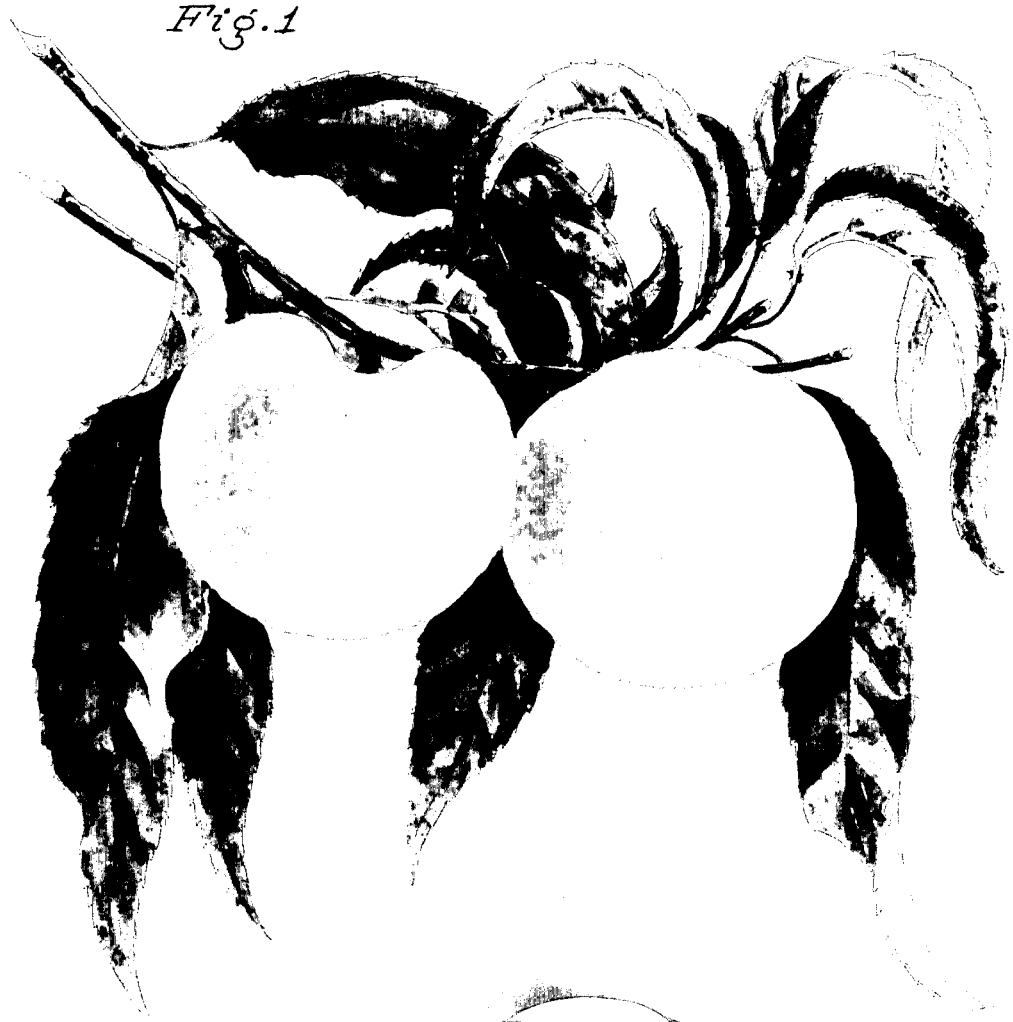
Fig. 1 is an elevation showing two of the fruit of the variety, together with twigs and leaves.
Figure 2:
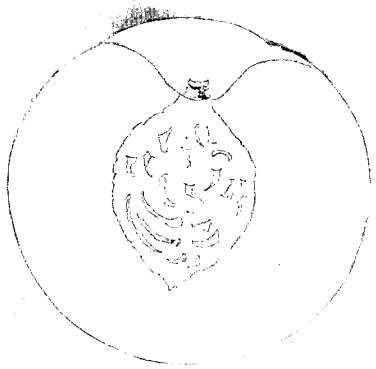
Fig. 2 is a sectional elevation of one of the fruits with the stone exposed.

Referring now more specifically to the pomological details of this new and distinct variety of nectarine tree, the following is an outline description thereof; all major color plate identifications being by reference to Maerz and Paul Dictionary of Color:

Tree: Large; vigorous. Upright to spreading. Regular and heavy producer.
Trunk: Rather stocky.
Branches: Rather stocky but fairly long.
*Color.*—Brown.
*Lenticels.*—Medium.
Leaves: Medium size, averaging 6½" in length and 1⅝" width. Lanceolate. Medium thickness. Smooth.
*Color.*—Top side—medium green (22–L–1 shading to 22–L–6). Under side—lighter green (22–K–1).

*Margin.*—Crenate.
*Petiole.*—Medium length. Medium thickness.
*Glands.*—Average two on petiole, two or three on blade. Medium size. Reniform. Stipules—none.
Flower buds: Medium size. Medium length.
Flowers:
*Dates of first and full bloom.*—Average, two or three days before the Elberta peach. Early to medium compared with other varieties. Large; showy.
*Color.*—Pink.
*Anthers.*—Red, producing viable pollen.
Fruit:
*Maturity when described.*—Eating ripe.
*Date of first picking.*—June 20, 1953.
*Date of last picking.*—July 3, 1953.
*Size.*—Uniform. Medium to large; relatively large for an early season nectarine. Average diameter axially—2½". Average transverse in suture plane—2½".
*Form.*—Uniform; symmetrical; globose.
*Suture.*—Shallow.
*Ventral surface.*—Rounded slightly. Strongly lipped.
*Cavity.*—Rounded, averaging ⅝" in depth and ⅞" in breadth. Markings red.
*Base.*—Rounded.
*Apex.*—Short.
Skin: Medium thickness. Medium tough. Tenacious to flesh.
*Tendency to crack.*—None.
*Down.*—Wanting.
*Color.*—Yellow (10–K–8) largely overlaid with red, including feathery red markings (2–J–11 shading to 3–L–11).
Flesh:
*Juice.*—Moderate.
*Texture.*—Firm.
*Ripens.*—Even.
*Flavor.*—Sub-acid to mild.
*Aroma.*—Not very pronounced.
*Eating quality.*—Very good.
*Color.*—Yellow (9–L–6 shading to 9–L–7), with reddish tinge (1–K–8) next to stone.
Stone: Free. Parts from flesh smoothly.
*Size.*—Medium to large. Average length—1⅝". Average breadth—1⅛". Average thickness—⅞".
*Form.*—Somewhat oblong.
*Hilum.*—Rather broad and oval.
*Apex.*—Acute.
*Sides.*—Equal.
*Surface.*—Irregularly furrowed and pitted throughout.
*Pits.*—Elongated.
*Ventral edge.*—Thin.
*Dorsal edge.*—Full, with narrow groove.
*Ridges.*—Continuous.
*Color.*—Light brown (3–A–10 shading to 4–G–10).
*Tendency to split.*—Very few split pits observed.
Use: Market; dessert.
Shipping quality: Good.
Keeping quality: Good.
Resistance to disease: No unusual susceptibility noted, and the usual spray practices have maintained under control those insects and diseases that are prevalent in the orchard areas of California.

The tree and its fruit herein described may vary in slight detail due to climatic and soil conditions under which the variety may be grown.

Having thus described the invention I claim:

A new and distinct variety of nectarine tree, as illustrated and described, characterized—in comparison to the John Rivers nectarine—by freestone fruit having a larger size, yellow flesh instead of white, firmer flesh, and more colorful exterior fruit color, but having substantially the same harvest period.

No references cited.